United States Patent
Herleikson et al.

(10) Patent No.: US 12,417,847 B1
(45) Date of Patent: Sep. 16, 2025

(54) SYSTEMS AND METHODS FOR RHYTHM RECOGNITION

(71) Applicant: Defibrio AS, Raadal (NO)

(72) Inventors: Earl Herleikson, Marion, MT (US); Arne Bergby, Rådal (NO); Joshua Hale, Arlington, MA (US)

(73) Assignee: Defibrio AS, Raadal (NO)

( * ) Notice: Subject to any disclaimer, the term of this patent is extended or adjusted under 35 U.S.C. 154(b) by 0 days.

(21) Appl. No.: 19/009,232

(22) Filed: Jan. 3, 2025

(51) Int. Cl.
*A61N 1/39* (2006.01)
*G16H 20/40* (2018.01)
*G16H 40/67* (2018.01)
*G16H 50/20* (2018.01)

(52) U.S. Cl.
CPC ............ *G16H 50/20* (2018.01); *A61N 1/3904* (2017.08); *A61N 1/3993* (2013.01); *G16H 20/40* (2018.01); *G16H 40/67* (2018.01)

(58) Field of Classification Search
None
See application file for complete search history.

(56) References Cited

U.S. PATENT DOCUMENTS

2011/0105930 A1* 5/2011 Thiagarajan ......... A61B 5/7217
600/523

* cited by examiner

*Primary Examiner* — Benjamin J Klein
*Assistant Examiner* — Willow Grace Welch
(74) *Attorney, Agent, or Firm* — DLA PIPER LLP (US)

(57) ABSTRACT

The disclosed systems and methods provide systems and methods for rhythm recognition and the analysis of ECG signals.

18 Claims, 9 Drawing Sheets

SYSTEMS AND METHODS FOR RHYTHM RECOGNITION

BACKGROUND OF THE DISCLOSURE

Electrocardiogram (ECG) signals are a pivotal tool in the field of medical technology, particularly in the diagnosis and monitoring of heart conditions. These signals are electrical recordings of the heart and can provide valuable information about the heart's rhythm and electrical activity.

One of the primary uses of ECG signals is in the detection of abnormal heart rhythms, known as arrhythmias. These can range from benign to life-threatening, and accurate detection is often paramount to appropriate treatment. Two particularly dangerous types of arrhythmias are Ventricular Tachycardia (VT) and Ventricular Fibrillation (VF).

VT is a rapid heart rhythm that originates from the ventricles, the lower chambers of the heart. Not all VTs are shockable, as some may still result in effective blood pumping. However, VT that originates from the ventricles can lead to ineffective blood pumping due to a circular electrical path in the ventricles. This can often degrade into VF if not corrected.

VF, on the other hand, is a condition where the ventricles have random waves of electrical activity, causing the muscle cells to work against each other and fail to pump blood. This can also occur when the ventricles trigger on their own, leading to rapid, persistent contractions without adequate time for the muscle cells to properly repolarize.

The analysis of ECG signals for the detection of these conditions is a complex task. Various techniques have been developed, including time domain, frequency domain, and time-frequency domain methods. These techniques aim to detect the QRS complex, a graphical deflection seen on an ECG that corresponds to the depolarization of the ventricles.

Automated External Defibrillators (AEDs) are devices that analyze ECG signals to determine whether a shock is recommended to correct an abnormal heart rhythm. These devices use algorithms to analyze heart rate, conduction, amplitude, and stability measures to make a shock decision.

Despite the advancements in ECG signal analysis and AED technology, the field continues to evolve, with ongoing research and development aimed at improving the accuracy and efficiency of these systems.

SUMMARY OF THE DISCLOSURE

According to one aspect of the present disclosure, a computing system can include a processor and a non-transitory computer-readable storage device storing computer-executable instructions, the instructions operable to causing the processor to perform operations. The operations can include receiving an electrocardiogram (ECG) signal from a mobile automated external defibrillator (AED) unit; filtering the ECG signal with a bandpass filter to generate an output signal; identifying two or more peaks in the output signal; calculating a cross-correlation energy for each of the two or more peaks; calculating a self-correlation energy for each of the two or more peaks; generating a correlation value for the ECG signal based on the cross-correlation energy and the self-correlation energy each of the two or more peaks; and determining, based on the correlation value, whether a shock is required.

In some embodiments, filtering the ECG signal comprises filtering the ECG signal with a first bandpass filter and a second bandpass filter. In some embodiments, the first bandpass filter operates between 6 and 18 Hz and the second bandpass filter operates between 14 and 26 Hz. In some embodiments, each of the first and second bandpass filters provide two outputs as the output signal. In some embodiments, each of the first and second bandpass filters generate a real signal and an imaginary signal. In some embodiments, calculating the cross-correlation energy comprises calculating a cross correlation energy between each peak and a plurality of other peaks of a same type.

In some embodiments, calculating the self-correlation energy can include calculating a self-correlation energy for each peak of a pair of peaks; multiplying the self-correlation energy for each peak; and generating a square root of the product. In some embodiments, generating the correlation value can include summing the cross-correlation energies; summing the self-correlation energies; and dividing the sum of the cross-correlation energies by the sum of the self-correlation energies. In some embodiments, the operations comprise administering a shock to a subject based on the generated correlation value. In some embodiments, the operations comprise causing a recommendation to be displayed on a user interface of a user device based on the generated correlation value.

According to another aspect of the present disclosure, a compute-implemented method performed by at least one processor can include receiving an electrocardiogram (ECG) signal from a mobile automated external defibrillator (AED) unit; filtering the ECG signal with a bandpass filter to generate an output signal; identifying two or more peaks in the output signal; calculating a cross-correlation energy for each of the two or more peaks; calculating a self-correlation energy for each of the two or more peaks; generating a correlation value for the ECG signal based on the cross-correlation energy and the self-correlation energy each of the two or more peaks; and determining, based on the correlation value, whether a shock is required.

In some embodiments, filtering the ECG signal comprises filtering the ECG signal with a first bandpass filter and a second bandpass filter. In some embodiments, the first bandpass filter operates between 6 and 18 Hz and the second bandpass filter operates between 14 and 26 Hz. In some embodiments, each of the first and second bandpass filters provide two outputs as the output signal. In some embodiments, each of the first and second bandpass filters generate a real signal and an imaginary signal. In some embodiments, calculating the cross-correlation energy comprises calculating a cross correlation energy between each peak and a plurality of other peaks of a same type.

In some embodiments, calculating the self-correlation energy can include calculating a self-correlation energy for each peak of a pair of peaks; multiplying the self-correlation energy for each peak; and generating a square root of the product. In some embodiments, generating the correlation value can include summing the cross-correlation energies; summing the self-correlation energies; and dividing the sum of the cross-correlation energies by the sum of the self-correlation energies. In some embodiments, the method can include administering a shock to a subject based on the generated correlation value. In some embodiments, the method can include causing a recommendation to be displayed on a user interface of a user device based on the generated correlation value.

BRIEF DESCRIPTION OF THE FIGURES

Various objectives, features, and advantages of the disclosed subject matter can be more fully appreciated with reference to the following detailed description of the disclosed subject matter when considered in connection with the following drawings, in which like reference numerals identify like elements.

The drawings are not necessarily to scale, or inclusive of all elements of a system, emphasis instead generally being placed upon illustrating the concepts, structures, and techniques sought to be protected herein.

Figure 1:
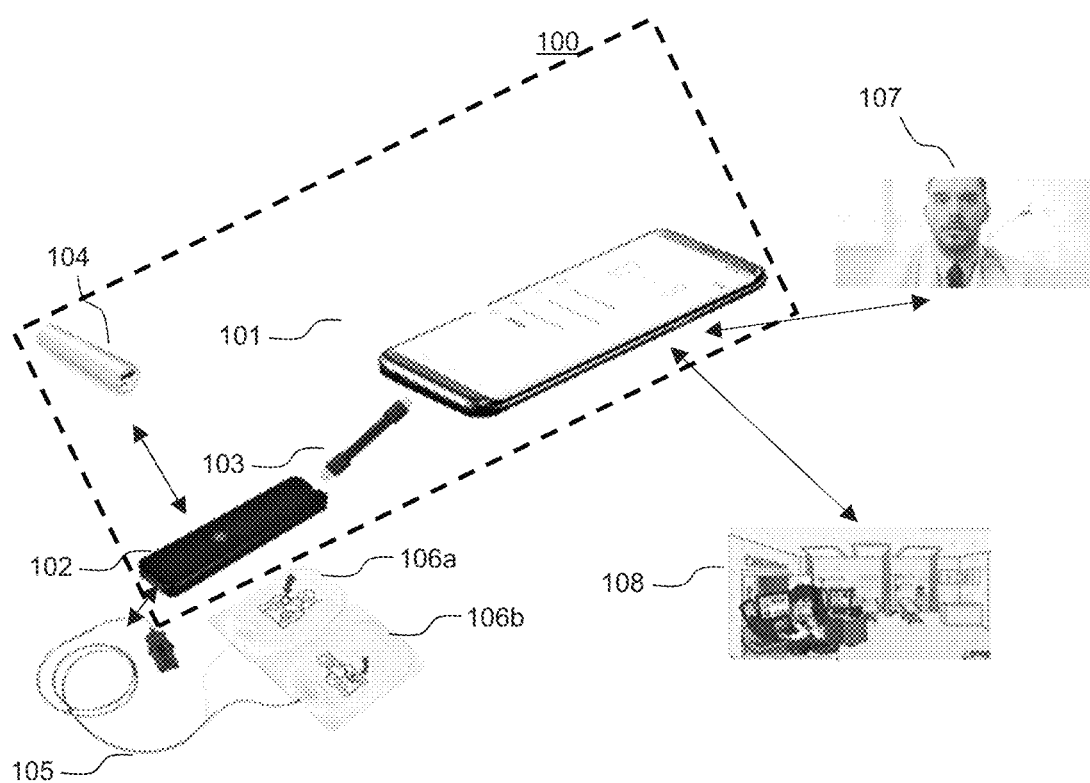
FIG. 1 is an example mobile automatic external defibrillator (AED) system according to some embodiments of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The structural components of the security system have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DESCRIPTION

The following detailed description is merely exemplary in nature and is not intended to limit the invention or the applications of its use.

In a human heart, a cardiac muscle cell slowly builds up a voltage potential between the inside and outside of the cell. This voltage is the potential energy of the muscle that allows the muscle to do work. When there is a change in voltage next to this cell, it can trigger the cell to depolarize. The depolarization of the cell is a rapid change in voltage as the potential between the inside and outside collapses in about 3-5 ms. After the muscle cell depolarizes, there is a pause of about 175 ms before the cell begins the repolarization process. The cell typically takes about 75 ms to repolarize. When the individual voltage changes of each cell are seen in aggregate as an ECG signal measured at the body surface, the heart muscle contraction is seen as a rapid change in voltage due to the 3-5 ms cellular response time. The repolarization of the heart is seen as a much slower change in voltage and usually much lower in amplitude due to the 75 ms cellular response time.

In a normal heartbeat, there is a wave of muscle cell depolarization from the bottom of the heart up towards the top as the heart muscle squeezes the blood out into the arteries. This is seen in the ECG waveform as the QRS complex. The QRS is seen as a rapid change in the ECG potential. The duration of this QRS depolarization wave is generally in the range 40 to 120 ms.

Generally, the focus of a shock advisory algorithm is to determine if the heart is effectively pumping blood. The ventricles contract in an organize fashion to pump blood. If the muscle cells are working together, there is a period of contraction (depolarization) followed by a period of relaxation and then repolarization followed by a wait for the signal from the top of the heart to start another contraction. When the ventricles have random waves of electrical activity such that some of the ventricle cells are depolarizing while some of the cells are re-polarizing, it is called VF. This results in a situation where the muscle cells are working against each other, and they fail to pump blood. In addition to VF, there is also condition where the ventricles are triggering on their own instead of being triggered by the top of the heart. This is called VT. In this case, the end of one contraction rapidly leads to a second contraction. If this happens in a persistent rapid fashion with every heartbeat, the ventricles may be operating in somewhat of an organized fashion but without adequate time for all the muscle cells to properly repolarize resulting in a heart that is not effectively pumping blood. This can then degrade into VF as the heart muscle cells are themselves not getting adequate blood supply to operate correctly.

The existing techniques for ECG signal analysis are many and varied. There are many applications where computer analysis and classification of ECG signals is employed. In general, measurements are usually performed in the time domain, or the frequency domain or in the time-frequency domain or some other type of transformation that helps to decompose the signal into an output that is sensitive to the detection of a QRS complex.

Embodiments of the present disclosure relate to systems and methods for rhythm recognition and the analysis of ECG signals. The disclosed systems and methods can utilize a combination of both frequency- and time-domain analysis to optimally and accurately differentiate between shockable and non-shockable heart rhythms. In particular, the disclosed principles can increase computational efficiency while increasing performance. For example, the disclosed systems and methods can utilize various bandpass filters that help make the system insensitive to artifacts and noise. Moreover, the system can deconstruct ECG waveforms into characteristics in an optimal manner for classifying depolarizations of the heart muscle. The disclosed systems and methods can also utilize peak detection methods, cross-correlation energy calculations, and self-correlation energy calculations to ultimately determine whether an ECG signal is shockable or non-shockable in a more accurate and efficient manner.

FIG. 1 is an example mobile AED system 100, according to some embodiments of the present disclosure. Mobile AED system 100 can include a defibrillator unit 102 removably connected via connection 103 to a device 101. Defibrillator unit 102 can include circuitry configured to generate specific pulses or shocks to administer to a patient for treating cardiac arrest victims. It is important to note that, while device 101 is a smartphone in this illustration of mobile AED system 100, this is not limiting. Device 101 could be other devices with an operating system capable of running an application, such as a tablet, laptop, computer, watch, or car entertainment system. In some embodiments, connection 103 can include a USB-C connection or other similar connections. Connection 103, when connecting device 101 and defibrillator unit 102, can allow for defibrillator unit 102 to be controlled via a user interface and application on device 101. In some embodiments, defibrillator unit 102 can optionally include an additional connection port to power bank 104 (e.g. portable charger, outlet, etc.), which can also be a USB-C port but may be different than the port for connection 103.

Defibrillator unit 102 can include an additional port for connection to a wire 105; wire 105 can act as a medium for which shocks determined and/or generated by circuitry within defibrillator 102 can be transferred to pads 106a-b. Pads 106a-b can be any standard defibrillator pads known in the art and can be configured to stick to a patient's body and operate as electrodes to feed current into a person's body from the defibrillator unit 102. In some embodiments, pads 106a-b can also include accelerometers. In some embodiments, the pads 106a-b can also include more intelligent sensing equipment, such as circuitry for ultrasound detection of blood flow and/or light sensors for oxygen saturation, which could be particularly helpful for self-rescue procedures. In some embodiments, when defibrillator unit 102 is connected or plugged into device 101, a user can connect to a video assistant specialist 107. In some embodiments, a team of specialists can work on call and can communicate with a user of the device. For example, if someone suddenly experiences cardiac arrest, a nearby person could connect the defibrillator unit 102 to device 101, navigate to the application (or the application can open automatically in response to connection), and select an option to immediately join a video session with a specialist, who can help the person administer a shock and/or CPR to the victim. In some embodiments, a person can also, via the application on device 101, connect to emergency services (e.g. call 911). In some embodiments, the application on the device 101 can be configured to be controlled remotely by emergency personnel or a mobile AED specialist. This can allow for, since the defibrillator unit 102 is controlled by the application on the device 101, emergency personnel to actually control and implement electrical shocks to a subject connected to the defibrillator unit 102. In some embodiments, defibrillator unit 102 can be configured to receive power from 220 V power sources or sockets or from 12 V sockets in a vehicle.

In some embodiments, the defibrillator unit 102 can be integrated into a vehicle. For example, the defibrillator unit 102 can be fully integrated, with the only visible part being long-wired pads (4 m or more), or it can be a modular defibrillator unit 102 similar to the original device that can either be connected to a mobile phone or the app on the car. This will make the defibrillator unit 102 more accessible for use in many situations.

In some embodiments, the mobile AED system 100 of FIG. 1 can be the same or similar to the devices described in U.S. Pat. Nos. 11,173,315 and 11,439,837, both of which are herein incorporated by reference in their entireties.

In some embodiments, the application on the device 101 can also be configured to receive data from external devices connected to user device 101, such as a smartwatch or other similar device that monitors the subject. For example, a person's smartwatch may consistently monitor their heartbeat and transmit this information to user device 101. In these embodiments, the effect of defibrillation can be improved using the signals from the smartwatch in addition to the pads 106a-b. Application 304 can be configured to monitor and analyze the subject's heartbeat and potentially identify and/or detect dangerous rhythms (e.g., rapid ventricular tachycardia, ventricular fibrillation, or other rhythm indicators that a neural network has been trained to detect). In response to detecting a dangerous rhythm, the application can be configured to notify the subject via device 101 and instruct them to connect their mobile AED and pads and potentially begin a self-rescue protocol.

In addition, the application on the device 101 can be configured to, via one or more processors on the mobile device 101, perform the processing techniques described in relation to FIGS. 3-7.

Figure 2:
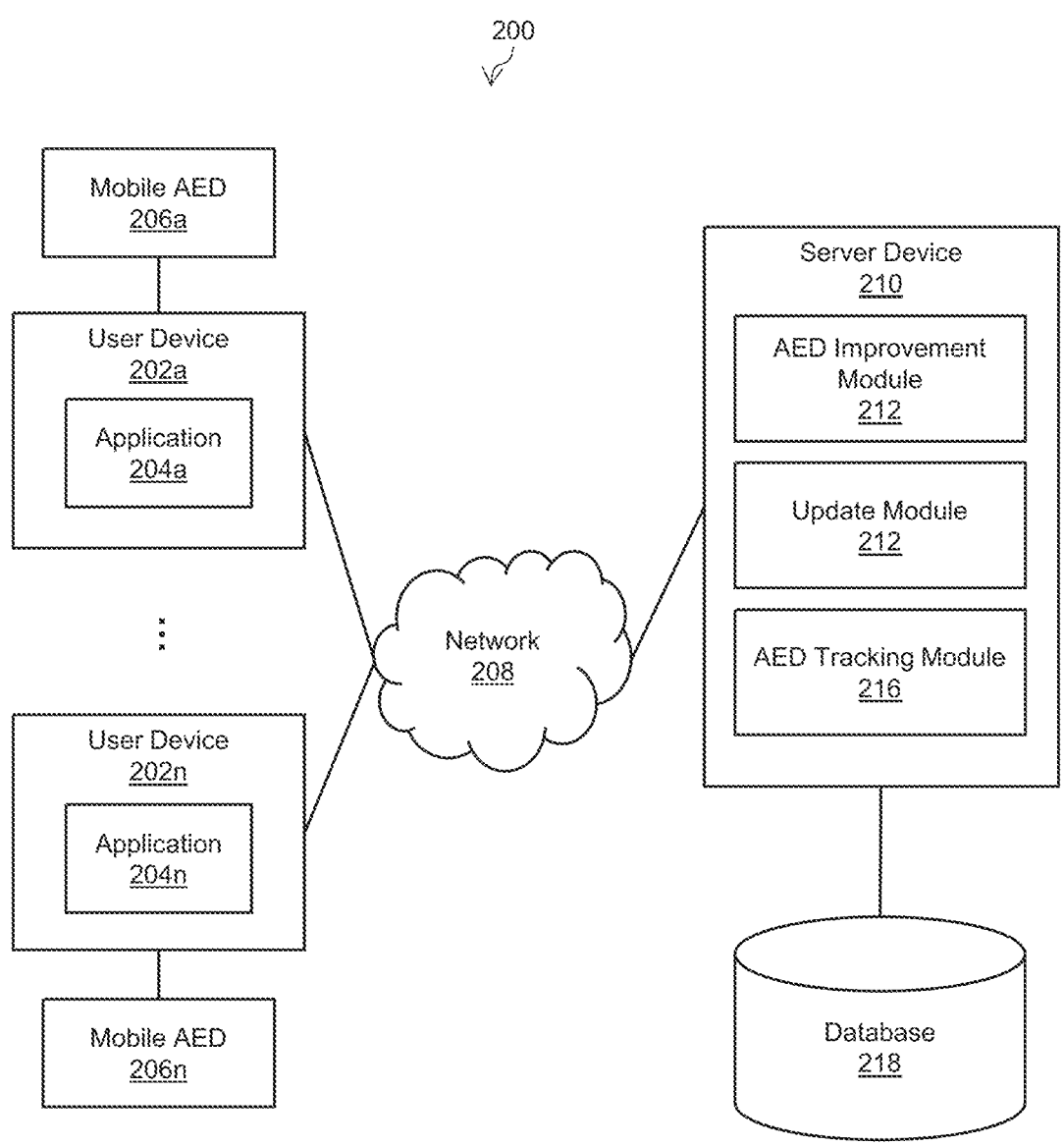
FIG. 2 is a block diagram of a system of mobile AED devices according to some embodiments of the present disclosure.

FIG. 2 is a block diagram of a system 200 of mobile AED devices according to some embodiments of the present disclosure. In some embodiments, system 200 can include a plurality of user devices 202a-n (user device 202 generally) communicably coupled to server device 210 via network 208. Note, system 200 includes two user devices 202a-n for illustrative purposes but any number of user devices can be included within the system of the present disclosure.

In some embodiments, network 208 may include one or more wide areas networks (WANs), metropolitan area networks (MANs), local area networks (LANs), personal area networks (PANs), or any combination of these networks. Network 208 may include a combination of one or more types of networks, such as Internet, intranet, Ethernet, twisted-pair, coaxial cable, fiber optic, cellular, satellite, IEEE 801.11, terrestrial, and/or other types of wired or wireless networks. Network 208 can also use standard communication technologies and/or protocols.

In some embodiments, a user device 202 can be similar to or the same as device 101 of FIG. 1. For example, user device 202 can include a smartphone, tablet, laptop, watch, car entertainment system, or a combination of similar types of devices that can run a software application and utilize an operating system. A user device 202 can include one or more computing devices capable of receiving user input as well as transmitting and/or receiving data via network 208 or communicating with server device 210. In some embodiments, user device 202 can include a conventional computer system, such as a desktop or laptop computer. Alternatively, user device 202 can include a device having computer functionality, such as a personal digital assistant (PDA) or other suitable device. Additionally, each user device 202 can include a specifically installed application 204 for use in conjunction with a connected mobile AED 206. Application 204 can include software instructions, which can be stored on a non-transitory computer readable medium, that, when executed by a processor (e.g. a processor within user device 202), can perform various processes related to administering shocks as an AED and reading EKGs in conjunction with a mobile AED 206.

In some embodiments, application 204 can include further instructions for reading a heartbeat of the patient as the defibrillator unit 206 is being charged. Instead of reading and analyzing the heartbeat, and then waiting until the device is fully charged, as conventional AED devices do, the disclosed embodiments can simultaneously implement the ability to charge the defibrillator unit 206 unit as it reads and analyzes the heartbeat. In this way an earlier shock can be applied when needed. The user device 202 will have the processing power to accomplish both tasks, and this will also be possible because there is full duplex communication (i.e., simultaneous communication in both directions) over USB-C while charging over the same cable. For example, at full duplex, a full-featured USB-C cable that implements USB 3.1 Gen. 2 can handle a data rate of up to ten Gbit/s. At the same time, there are separate lines within USB-C for charging (Vbus), so that one device can send charging power on one line within the cable while communicating both ways at full speed on other lines in the same cable. In effect, the user device 202 can receive and interpret electrical signal information from the pads (e.g., pads 106) while charging. This will both improve the resulting treatment, as a deeper, and online assisted analyze of the signal can be performed, over a longer period of time than a traditional AED.

Server device 210 may include any combination of one or more of web servers, mainframe computers, general-purpose computers, personal computers, or other types of computing devices. Server device 210 may represent distributed servers that are remotely located and communicate over a communications network, or over a dedicated network such as a local area network (LAN). Server device 210 may also include one or more back-end servers for carrying out one or more aspects of the present disclosure. In some embodiments, server device 108 may be the same as or similar to server device 800 described below in the context of FIG. 8.

As shown in FIG. 2, server device 210 can include an AED improvement module 212, an update module 214, and an AED tracking module 216. Additionally, server device 210 can be communicably coupled to a database 218. In some embodiments, AED improvement module 212 can include one or more models/algorithms trained via machine learning that can be used to continuously improve AED and/or CPR performance overtime. In some embodiments, AED improvement module 212 can be configured to continuously receive performance data from user devices 202 and retrain or update models to reflect newly received performance data. In some embodiments, AED improvement module 212 can also have access to Emergency Health Records and other external databases to obtain additional training data. In some embodiments, AED improvement module 212 can be configured to analyze, retrain, and/or update various machine learning models related to AED performance, such as models that determine lengths and levels of initial pulses, pad placement, body part detection, how often to provide additional pulses, the amount of energy in each pulse, and various other decisions related to electrocardiogram (EKG) readings. In some embodiments, the decisions can also be made based on other data related to the use of the mobile device interface, such as time spent on different screens, the number of times the back function is used, general timing of use, etc., to improve and optimize the user experience.

In some embodiments, update module 214 can be configured to package or incorporate updated/retrained models from AED improvement module 212 into a software update and distribute the update to the user devices 202. In some embodiments, the update may be received by user device 202 via download from an application store. In addition, AED tracking module 216 can be configured to track locations of each mobile AED 206. In some embodiments, AED tracking module 216 can utilize GPS coordinates (or any positioning signal) obtained from user device 202. In some embodiments, AED tracking module 216 can allow for a user to, via the application 204 on a user device 202, search for nearby mobile AEDs 206.

Figure 3:
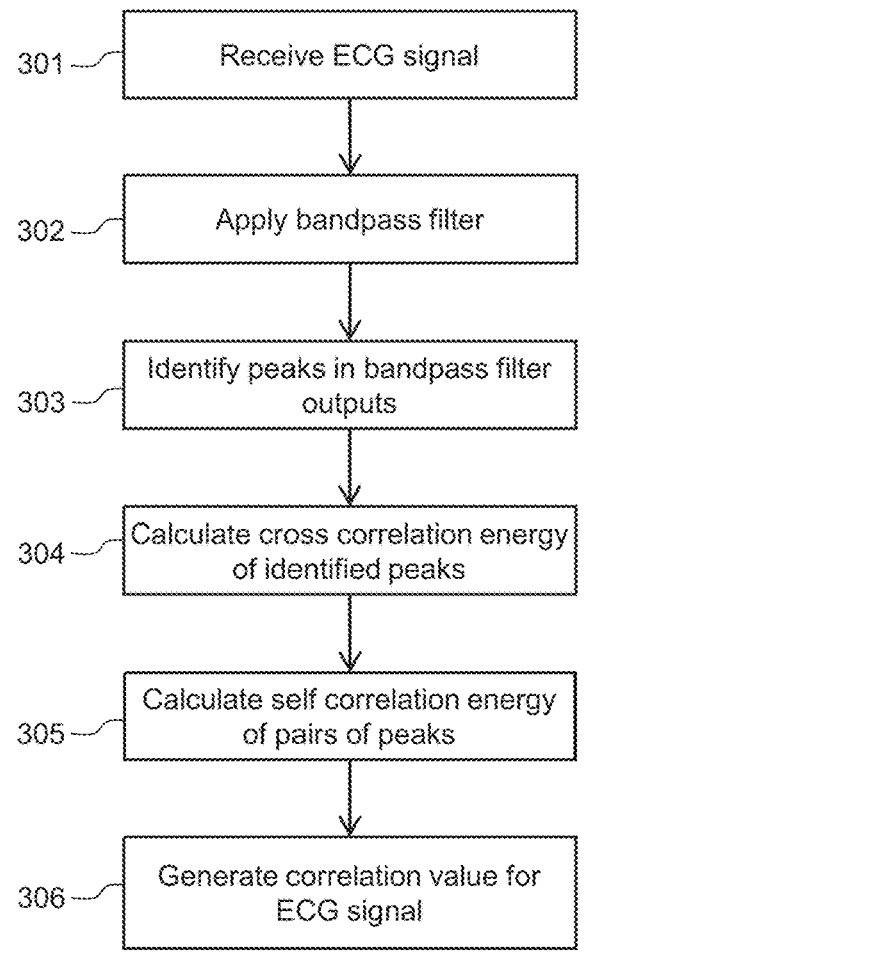
FIG. 3 is an example process for determining a shockable rhythm according to some embodiments of the present disclosure.

FIG. 3 is an example process 300 for determining a shockable rhythm according to some embodiments of the present disclosure. In some embodiments, the process 300 can be performed by the application 204 executing on the user device 202. In other words, the processor on the user device 202 can execute the processes described herein, although this is not limiting. In some embodiments, a microcontroller on a mobile AED 206 could also perform one or more of the disclosed processes. In some embodiments, process 300 can be performed after various electrodes 106 have been connected to a subject and the mobile AED 206 has been connected to the user device 202.

At block 301, the process 300 can include receiving an ECG signal from the mobile AED 206. For example, the electrodes 106 are configured to capture ECG signals from a heart of the subject. These signals are then received so that they can be analyzed, either by the user device 202 or the mobile AED 206. At block 302, the process 300 can include applying a bandpass filter to the received ECG signals. As discussed above, the use of bandpass filters can allow the system to be less sensitive to artifacts and noise. Moreover, the deconstructed signals created by the bandpass filters are useful for classifying depolarizations of the heart muscle. In some embodiments, two bandpass filters can be used. Each bandpass filter can have two outputs where one output is more responsive to the slope (both positive and negative) of the ECG signal and the other can be more responsive to the change in slope polarity representing a positive or negative peak of the waveform. This allows the bandpass filter to filter outputs that are responsive to positive and negative slopes and positive and negative peaks. In some embodiments, each bandpass filter can operate at approximately 10 Hz and 20 Hz. In some embodiments, one of the outputs (e.g., the output sensitive to slope) can be treated as an imaginary output and the other output (e.g., the output sensitive to change in slope polarity) can be treated as a real output. Additional details related to the bandpass filtering steps are discussed in relation to FIG. 4.

At block 303, the process 300 can include identifying one or more peaks in the outputs of the bandpass filter. In some embodiments, this can include detecting both positive and negative peaks in both the real and imaginary outputs. In addition, this can include identifying an overall maximum peak of all identified peaks. In some embodiments, by analyzing positive and negative real and imaginary peak amplitudes, the disclosed process can be sensitive to both normal ECG heartbeats and irregular heart activity as seen in VF. Additional details related to peak detection techniques are discussed in relation to FIG. 5.

At block 304, the process 300 can include calculating a cross-correlation energy of the peaks identified at block 303. In some embodiments, calculating the cross-correlation energy can include calculating a cross-correlation energy between each maximum peak and all other peaks of the same type (e.g., positive real, negative real, positive imaginary, negative imaginary). In some embodiments, the cross-correlation energy values can be calculated over a pre-defined time window, such as +/−100 ms. At block 305, the process 300 can include calculating a self-correlation energy of the peaks identified at block 303. In some embodiments, this can include calculating a self-correlation energy for each pair of peaks, such as by multiplying the self-correlation energy of each and taking the square root of the product. In some embodiments, such correlation calculations can be an improvement because typical correlation calculations are performed in a manner where the signals are shifted sample by sample across the entire block of data looking for maximums in the correlation. As described herein, by timing the correlation calculation to identified peaks, a correlation measure can be determined for each pair of peaks. Additional details related to cross-correlation and self energy calculations are discussed in relation to FIG. 6.

At block 306, the process 300 can include generating a correlation value for the ECG signal. In some embodiments, the correlation value can be generated based on the various correlation energies calculated herein. In some embodiments, generating the correlation value for an ECG signal can include summing the cross-correlation energies and dividing by the sum of the self-correlation energies. In some embodiments, the correlation value can have a value between zero and one. For example, in some embodiments, there can be little change in correlation value between 0.8 and 0.9, yet the 0.9 value of correlation can be about twice as good as the 0.8 value. In some embodiments, to amplify the differences of correlation for waves at higher levels of correlation, the inverse of the correlation can be used. In some embodiments, to prevent the inverse from approaching infinity, 1/(1.05−correlation) can be used. In some embodiments, the logarithm can be used as an alternative to inverse. In addition, the log function can also be a good way to enhance values close to 1. For example, a correlation metric of −ln(1.001−correlation) can be used. The inverse correlation of the individual pairs of peaks can then be weighted by the self-correlation and the ratio of the amplitudes of the peaks and then summed. This sum can be divided by the sum of the self correlated energy to arrive at a single value that represents the total inverse correlation of the entire block of ECG data. In some embodiments, the correlation value can indicate whether the ECG signal is consistent or random, which can be a key measure for detection of a VF waveform. Additional details related to generating the correlation value are discussed in relation to FIG. 7.

In some embodiments, the process 300 (in particular, the correlation value generated at block 306) can be used to make a decision to recommend delivering or not delivering a shock to the subject. For example, in some embodiments, an automatic determination based on the value of the correlation value could be made that determines that a shock is necessary, and then the shock is administered to the subject. In other embodiments, after the determination that a shock is necessary is made, a recommendation could be displayed via the application on the user device. The recommendation can indicate to the user that a shock should be administered to the subject, for example by pressing a button displayed on the user interface.

Figure 4:
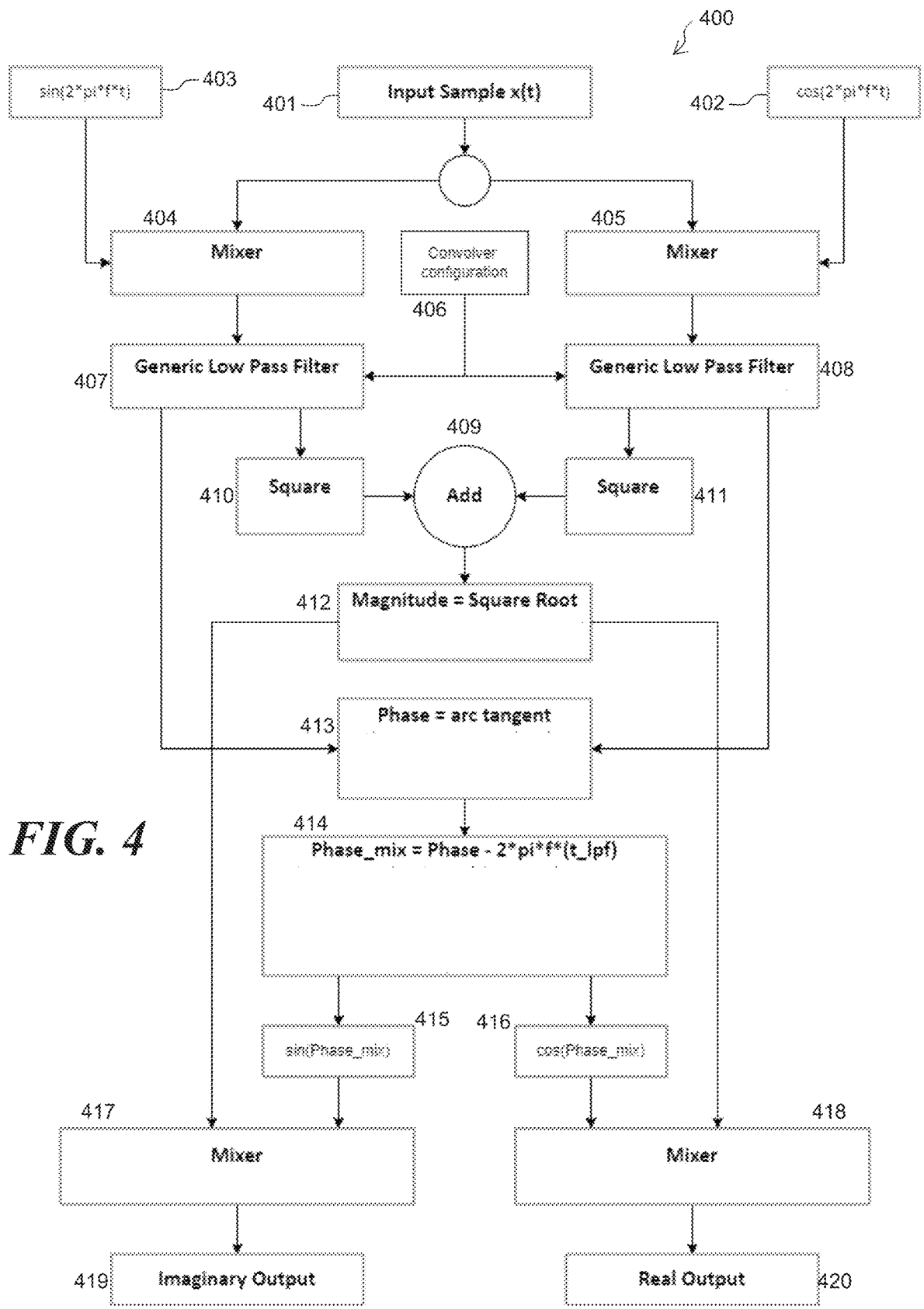
FIG. 4 is an example bandpass filter process that can be performed within the process of FIG. 3 according to some embodiments of the present disclosure.

FIG. 4 is an example bandpass filter process 400 that can be performed within the process of FIG. 3 according to some embodiments of the present disclosure. For example, the process 400 can be performed at block 302 of process 300. At block 401, the bandpass filter receives an input sample: the ECG signal from the mobile AED unit. The input sample can be fed to two mixers at 404 and 405. The mixer at 404 can receive a sin function 403 and add it to the input signal. In addition, the mixer at 405 can receive a cos function 402 and add it to the input signal. The output of the mixer at 404 can be fed to a generic low pass filter at 407, and the output of the mixer at 405 can be fed to a generic low pass filter 408. In some embodiments, each of the low pass filters 407 and 408 can be managed by a convolver configuration at 406. For example, one method of creating a low pass filter can be with a finite impulse response (FIR) filter. The implementation of a FIR filter can be performed by convolving the input data with the coefficients of the FIR filter. The convolver configuration, at 406, can define the FIR filter implementation. In some embodiments, the characteristics of the FIR low pass filter can be used to define the frequency response and time domain response of the bandpass filter. There can be a tradeoff between frequency response and time domain response. A wide bandwidth filter will be more responsive in the time domain but less capable of rejecting unwanted out of band signals. Additionally, a FIR low pass filter with a perfect notch at the mixer frequency can be very effective at removing DC and baseline wander. These are filter design characteristics that can be tuned for optimal performance in the detection of shockable waveforms.

Moreover, each of the low pass filters at 407 and 408 can have outputs that are fed to respective squaring steps at 410 and 411, where the output is squared and then sent to an adder at 409, which adds the squares from 410 and 411 together.

The added squares from 409 can then be fed to 412, where the square root of the sum (i.e., the output from the adder at 409) is calculated. In some embodiments, this value can be treated as a magnitude of the original ECG signal. In some embodiments, when the duration of the QRS complex is similar to the period of the mixer frequency, the output of 412 can be representative of the amplitude of the QRS. In addition, the output from 412 can be fed to mixers at 417 and 418.

In some embodiments, a second output from each of the low pass filters 407 and 408 can be fed to 413, where the unwrapped arc tangent of the second outputs is calculated. In some embodiments, this value can be used as the phase of the ECG signal. The phase can be fed as an input to 414, where a real and imaginary deconstruction can be performed. For example, at 414, a time-delay component can be subtracted from the phase to determine a phase mix. The output of 414 (the phase mix) can be fed to a sin function at 415 and a cos function at 416. The output of the sin function at 415 can be fed to a mixer 417, which mixes the output of the sin function 415 and the magnitude that was generated at 412, such as by addition. Similarly, the output of the cos function at 416 can be fed to a mixer 418, which mixes the output of the cos function 416 and the magnitude that was generated at 412, such as by addition. The output from the mixer 417 can be used as an imaginary output at 419 and the output from the mixer 418 can be used as a real output at 420.

Figure 5:
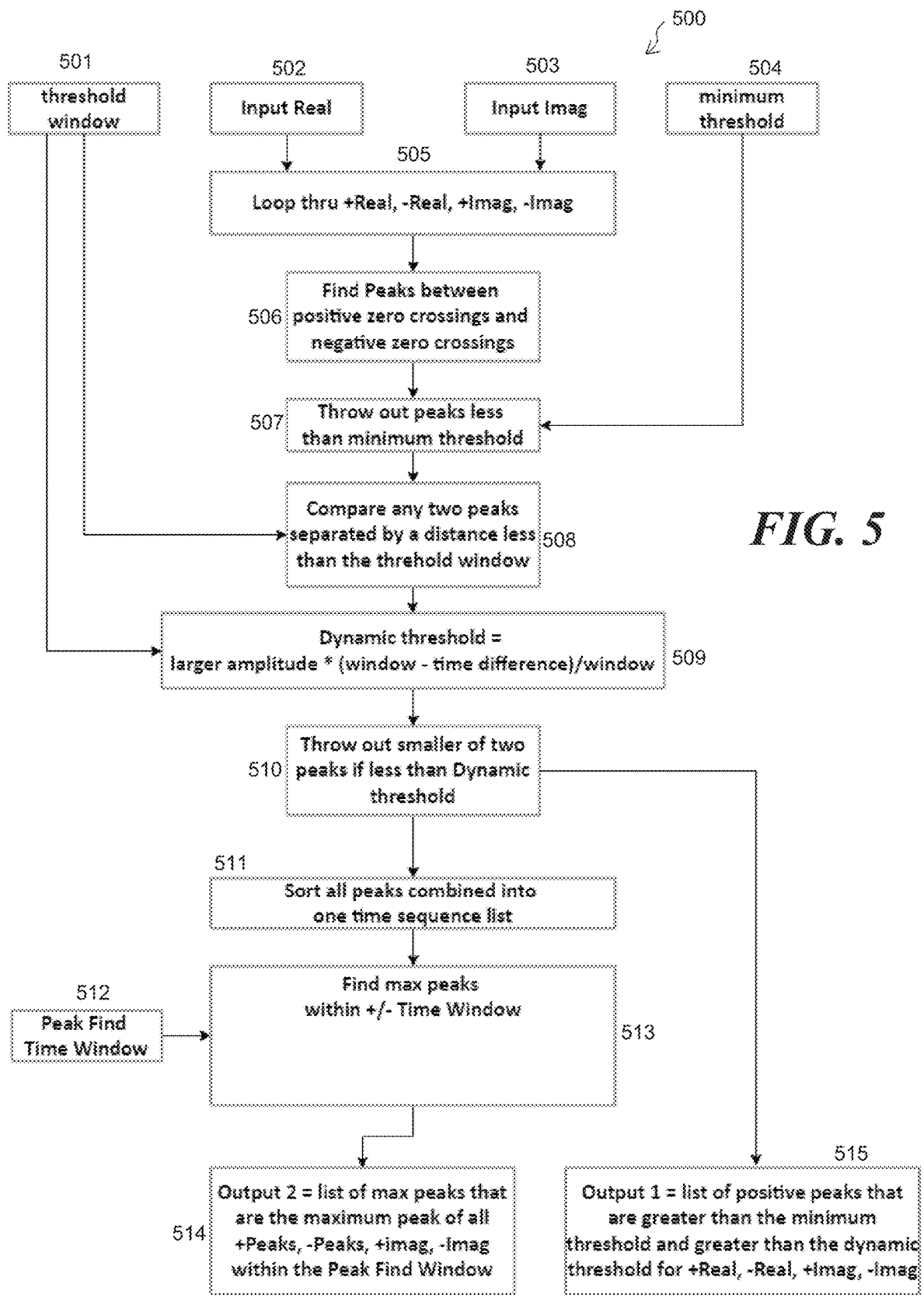
FIG. 5 is an example process for identifying peaks according to some embodiments of the present disclosure.

FIG. 5 is an example process 500 for identifying peaks according to some embodiments of the present disclosure. In some embodiments, the process 500 can be performed at block 303 of FIG. 3. In some embodiments, the real input at block 502 can be the real output from 420 of process 400. Likewise, the imaginary input 503 can be the imaginary output from 419 of process 400. The real and imaginary inputs from 502 and 503 can be fed to a looping step at 505, looping between positive and negative is performed for both the real and imaginary values. For example, at block 505, blocks 506-510 can be applied to +Real data, −Real data, +Imag data, and −Imag data As a result of the looping at 505, peaks between positive zero crossings and negative zero crossings can be found at 506. At 507, identified peaks can be discarded if they are less than a predefined minimum threshold, which is defined by the input 504. In addition, at 508, the process 500 can include comparing any two peaks separated by a distance less than a threshold window, which is defined by the input 501.

The output leads to 509, where a dynamic threshold is calculated by multiplying the larger amplitude by the predefined time window from 501 minus the time difference between the two peaks, and the difference is divided by the predefined time window. At 510, the smaller of the two peaks can be discarded if it is less than the dynamic threshold calculated at 509. The remaining peaks can then be passed to 511, where they are sorted and combined into a one-time sequence list. In some embodiments, the list of +Real peaks can be combined with the list of −Real peaks, +Imag peaks, and −Imag peaks. In some embodiments, this list can be sorted into a time-sequenced list. The sorted sequence list can then be fed to 513, where maximum peaks within a predefined peak find time window (defined by input 512) are identified. For example, peaks that have been identified but are less than the predefined peak time window from the start or end of the ECG signal are not included. In some embodiments, for each peak in the sorted list, if there is another peak within +/−"time window" that is larger, then this peak may not be included in the list of max peaks. Furthermore, if the start or end of the ECG data being analyzed is withing +/−"time window" then this peak may not be included either. The output can then be passed to 514, which generates a list of maximum peaks which includes the maximum positive and negative real and imaginary peaks within the predefined peak find time window. In addition, the output from 510 can be passed to 515, where another list is created that includes the positive peaks that are greater than a minimum threshold (defined by 504) and greater than the dynamic threshold generated at 509.

Figure 6:
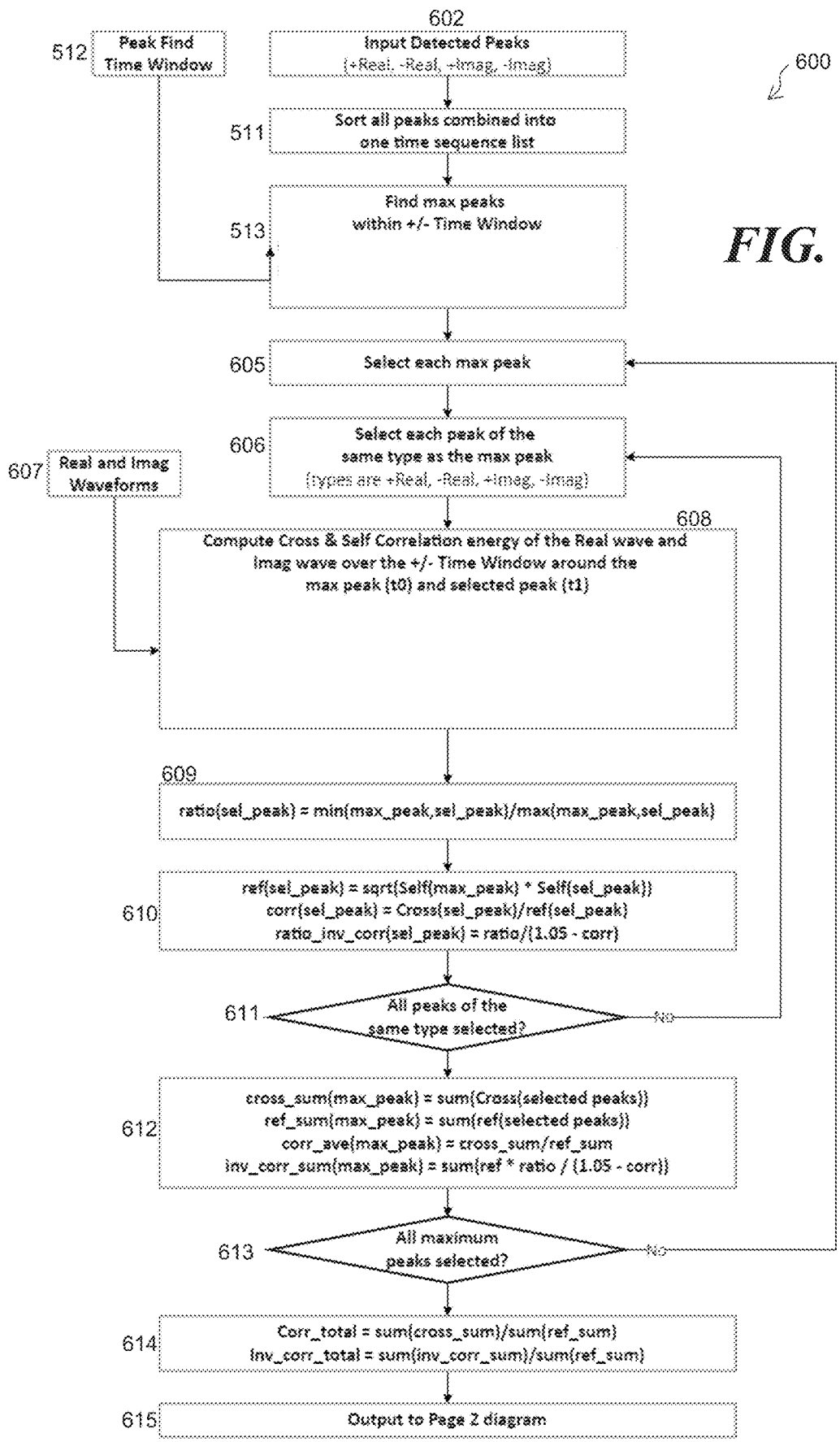
FIG. 6 is an example process for calculating correlation energies according to some embodiments of the present disclosure.

FIG. 6 is an example process 600 for calculating correlation energies according to some embodiments of the present disclosure. In some embodiments, the process 600 can be performed at blocks 304 and 305 of process 300. At block 602, the identified peaks (e.g., from block 303 and/or process 500, specifically block 510 and/or 514) are provided as an input. In some embodiments, providing the identified peaks as an input can include providing both positive and negative peaks of the real and imaginary portions of the ECG signal.

The inputs from 602 can be passed to 605, where each maximum peak is selected and fed to 606, where each peak of the same type as the maximum selected peak is selected from the 515 output and sent to 608. At 608, the process 600 can include computing a cross-correlation and a self-correlation energy. For example, a cross-correlation and a self-correlation energy can be computed of the real signal and the imaginary signal (which are received from 607). In some embodiments, the cross-correlation and self-correlation energy can be computed within a predefined time window around the maximum peak (t0) and the selected peak (t1). Example equations for the cross-correlation and self-correlation energy $$\text{Cross} = \sum_{-window}^{+window} (\text{real}(t+t0) * \text{real}(t+t1) + \text{imag}(t+t0) * \text{imag}(t+t1)) \quad (1)$$

$$\text{Self(sel\_peak)} = \sum_{-window}^{+window} \left(\text{real}(t+t1)^2 + \text{imag}(t+t1)^2\right) \quad (2)$$

$$\text{Self(max\_peak)} = \sum_{-window}^{+window} \left(\text{real}(t+t0)^2 + \text{imag}(t+t0)^2\right) \quad (2)$$

At 609, an amplitude ratio can be calculated as a measure of the relative size comparison between the max_peak and the sel_peak amplitudes, for example via equation (3) below.

$$\text{ratio}(sel_{peak}) = \min(\text{max\_peak}, sel\_\text{peak})/\max(\text{max\_peak}, sel\_\text{peak}) \quad (3)$$

At 610, a maximum possible value from a cross-correlation energy can be calculated. In some embodiments, Ref (sel_peak) can be the maximum possible value from a cross correlation energy calculation. The value can combine the self-correlation energy of both the max peak and the selected peak into a single value. If the max peak waveform is perfectly correlated with the selected peak waveform, then the Ref(sel_peak) can be equal to the Cross(sel_peak) which would produce a correlation value of one. Anything less than a perfect correlation will produce a cross correlation less than one. In some embodiments, Correlation=corr(sel_peak) =cross correlation energy divided by the combined self-correlation energy of the two waves. In some embodiments, the ratio_inv_corr(sel_peak) can take into account the relative difference in amplitude of the two peaks when calculating the inverse of the correlation. If the two peaks are substantially different in amplitude, it can reduce the inverse correlation value accordingly. A normal heartbeat will have very similar amplitudes from beat to beat. In another embodiment, ratio_inv_corr(sel_peak)=ratio/(1.05−corr) is replaced with ratio_log_corr(sel_peak)=−ratio*ln(1.001−corr).

In some embodiments, once all the selected peaks (of the same type as the given max peak) have been processed for correlation with the max peak, the correlation numbers can be summed to produce combined measures of correlation for each max peak. The average correlation (corr_ave) of a max peak with all the selected peaks can be the sum of all the cross-correlation-energy values divided by the sum of the self-correlation energy values. It is important to note that waves that are well correlated with larger values can be weighted heavier in the corr_ave calculation than waves with poor correlation or waves with smaller amplitudes.

In some embodiments, Inv_corr_sum(max_peak) can be the sum of all ratio_inv_corr(sel_peak) scaled by ref (sel_peak) which is the combined self-correlation energy of each peak. Later when inv_corr_total is calculated, the sum of all the ref values can be divided out. This can reflect a weighted average of the inverse correlation. Inverse correlation values where ref(sel_peak) is large are calculated from large amplitude waves and can have more impact on the average of the inverse correlation. In some embodiments, once all the max peaks are processed, a combined total correlation can be calculated. This is simply the sum of the cross_sum divided by the sum of the ref_sum. Again, for this average total measure of correlation between peaks of all types can be weighted toward the peaks with higher amplitudes and higher correlations.

Figure 7:
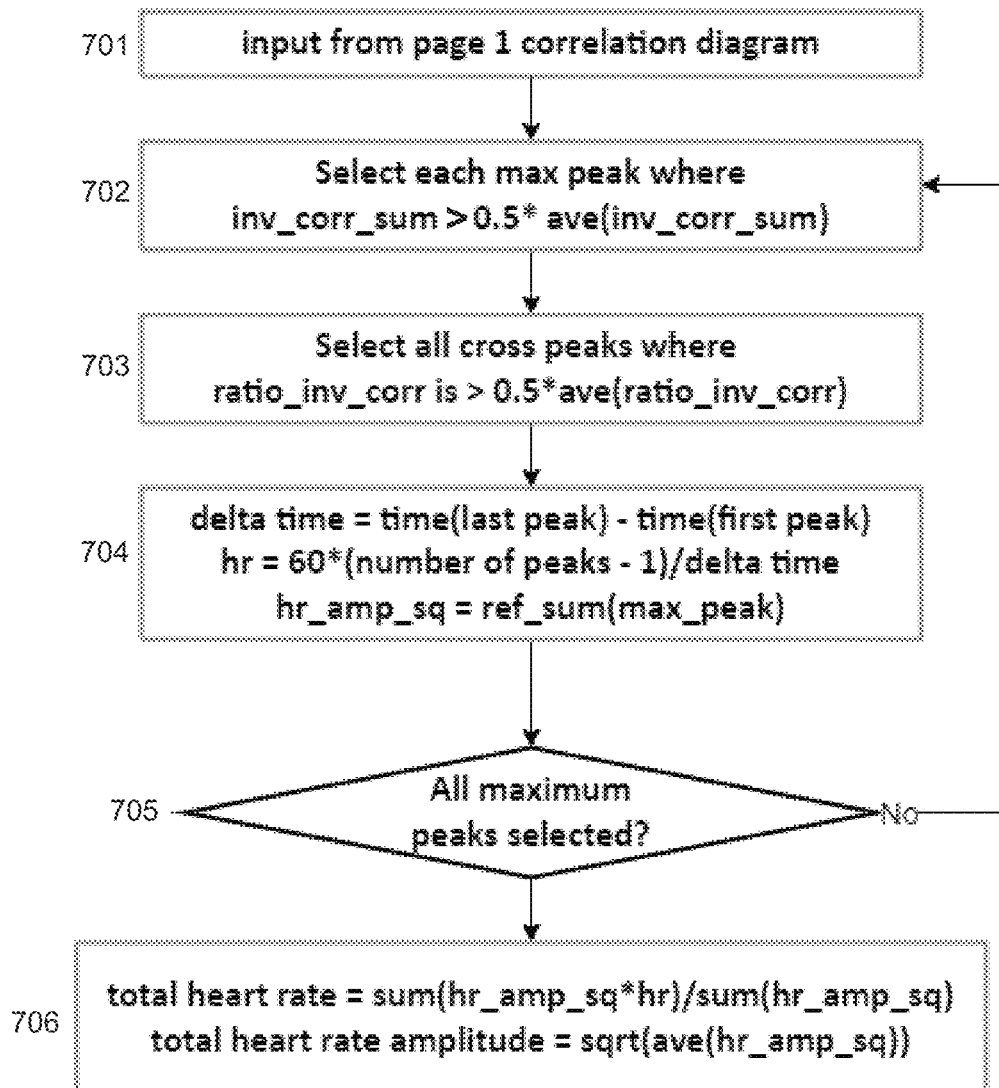
FIG. 7 is an example process for calculating a heart rate and amplitude according to some embodiments of the present disclosure.

FIG. 7 is an example process 700 for calculating a heart rate and amplitude according to some embodiments of the present disclosure. At block 701, the process 700 can include receiving peaks and the computed values for each peak from process 600. At block 702, max peaks with inverse correlations greater than 50% of the average are considered for heart rate calculations. Similarly, at block 703, only cross peaks with inverse correlations greater than 50% of the average are considered for heart rate calculations. At block 704, the process 700 can include calculating a time delta between the last peak and the first peak and calculating a ref sum of the max peaks. At block 705, the process 700 can include confirming that all maximum peaks have been selected. At block 706, the total heart rate can be calculated by dividing the sum of squared heartrate amplitudes * hours by the sum of squared heartrate amplitudes. Moreover, the total heart rate amplitude can be calculated by taking the square root of the sum of squared heartrate amplitudes. In some embodiments, log correlations can be used instead of inverse correlations in the calculation of heart rate and heart rate amplitude.

Additional Features

In some embodiments, the disclosed computing system can use a bandpass filter provides two or more outputs as the output signal.

In some embodiments, the disclosed computing system can use outputs that are the real and imaginary outputs of the bandpass filter.

In some embodiments, the outputs are the positive real, negative real, positive imaginary and negative imaginary outputs of the bandpass filter.

In some embodiments, one output is responsive to the slope of the ECG signal and another output is responsive to the peak of the ECG signal.

In some embodiments, one output is responsive to the positive slope of the ECG signal and another output is responsive to the negative slope of the ECG signal and another output is responsive to the positive peak of the ECG signal and another output is responsive to the negative peak of the ECG signal.

Figure 8:
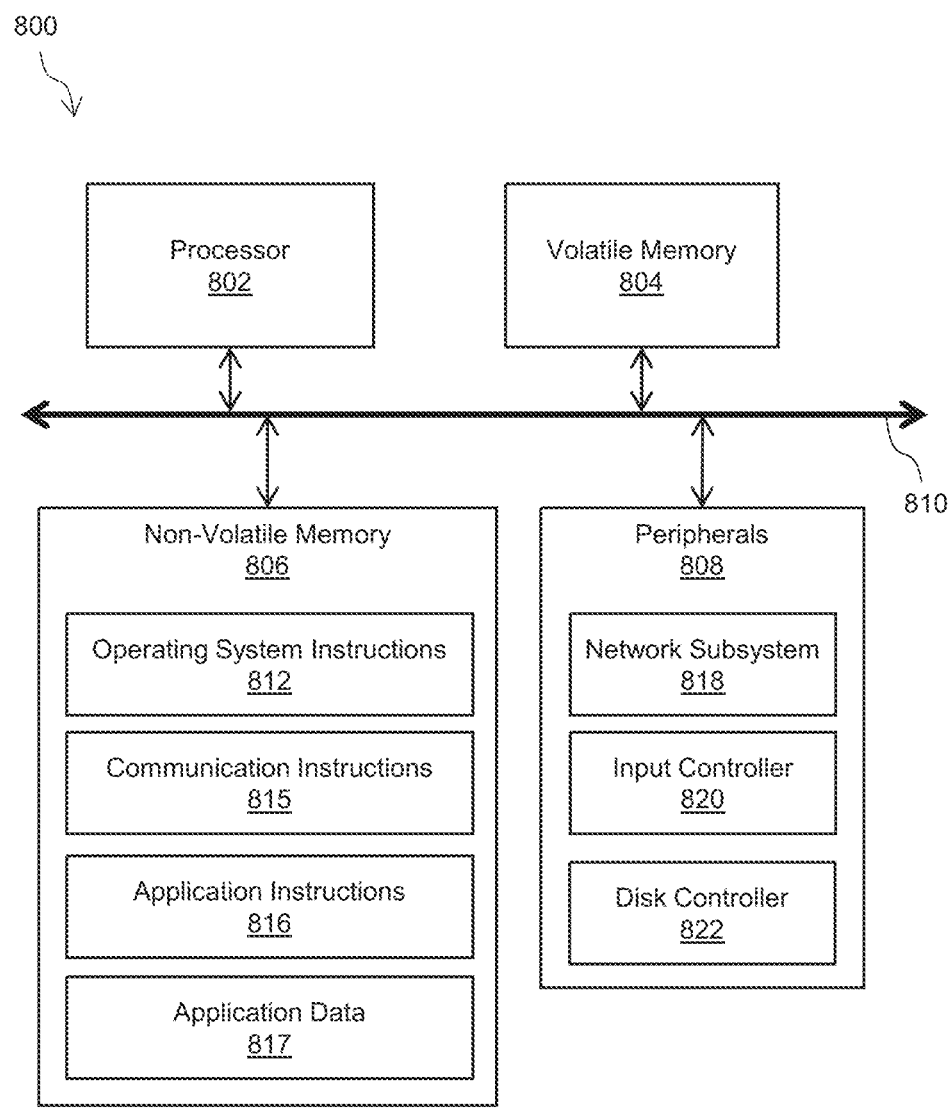
FIG. 8 is an example server device that can be used within the system of FIG. 2, according to some embodiments of the present disclosure.

FIG. 8 is an example server device 800 that can be used within the system of FIG. 2, according to some embodiments of the present disclosure. Server device 800 may implement various features and processes as described herein. Server device 800 may be implemented on any electronic device that runs software applications derived from complied instructions, including without limitation personal computers, servers, smart phones, media players, electronic tablets, game consoles, email devices, etc. In some implementations, server device 800 may include one or more processors 802, volatile memory 804, non-volatile memory 806, and one or more peripherals 808. These components may be interconnected by one or more computer buses 810.

Processor(s) 802 may use any known processor technology, including but not limited to graphics processors and multi-core processors. Suitable processors for the execution of a program of instructions may include, by way of example, both general and special purpose microprocessors, and the sole processor or one of multiple processors or cores, of any kind of computer. Bus 810 may be any known internal or external bus technology, including but not limited to ISA, EISA, PCI, PCI Express, NuBus, USB, Serial ATA, or Fire Wire. Volatile memory 804 may include, for example, SDRAM. Processor 802 may receive instructions and data from a read-only memory or a random access memory or both. Essential elements of a computer may include a processor for executing instructions and one or more memories for storing instructions and data.

Non-volatile memory 806 may include by way of example semiconductor memory devices, such as EPROM, EEPROM, and flash memory devices; magnetic disks such as internal hard disks and removable disks; magneto-optical disks; and CD-ROM and DVD-ROM disks. Non-volatile memory 806 may store various computer instructions including operating system instructions 812, communication instructions 815, application instructions 816, and application data 817. Operating system instructions 812 may include instructions for implementing an operating system (e.g., Mac OS®, Windows®, or Linux). The operating system may be multi-user, multiprocessing, multitasking, multithreading, real-time, and the like. Communication instructions 815 may include network communications instructions, for example, software for implementing communication protocols, such as TCP/IP, HTTP, Ethernet, telephony, etc. Application instructions 816 may include instructions for administering shock patterns using a mobile AED, connecting to law enforcement, displaying instructions for administering shock patterns using the mobile AED, and performing a self-rescue operation according to the systems and methods disclosed herein.

Peripherals 808 may be included within server device 800 or operatively coupled to communicate with server device 800. Peripherals 808 may include, for example, network subsystem 818, input controller 820, and disk controller 822. Network subsystem 818 may include, for example, an Ethernet of WiFi adapter. Input controller 820 may be any known input device technology, including but not limited to a keyboard (including a virtual keyboard), mouse, track ball, and touch-sensitive pad or display. Disk controller 822 may include one or more mass storage devices for storing data files; such devices include magnetic disks, such as internal hard disks and removable disks; magneto-optical disks; and optical disks.

Figure 9:
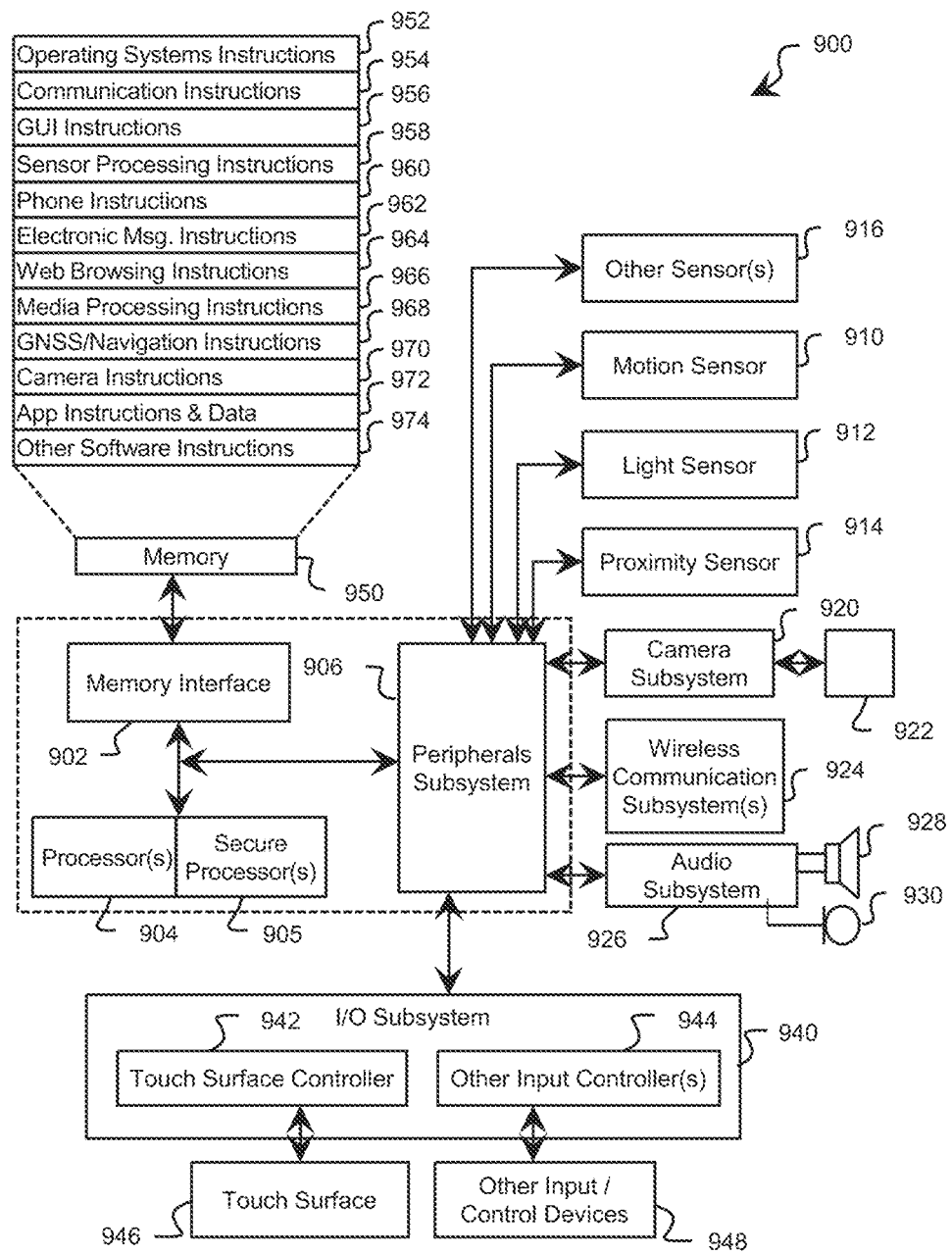
FIG. 9 is an example computing device that can be used within the system of FIG. 2 according to some embodiments of the present disclosure.

FIG. 9 is an example computing device 900 that can be used within the system of FIGS. 1 and/or 3, according to some embodiments of the present disclosure. In some embodiments, device 900 may be user device 101. The illustrative user device 900 may include a memory interface 902, one or more data processors, image processors, central processing units 904, and/or secure processing units 905, and peripherals subsystem 906. Memory interface 902, one or more processors 904 and/or secure processors 905, and/or peripherals subsystem 906 may be separate components or may be integrated in one or more integrated circuits. The various components in user device 900 may be coupled by one or more communication buses or signal lines.

Sensors, devices, and subsystems may be coupled to peripherals subsystem 906 to facilitate multiple functionalities. For example, motion sensor 910, light sensor 912, and proximity sensor 914 may be coupled to peripherals subsystem 906 to facilitate orientation, lighting, and proximity functions. Other sensors 916 may also be connected to peripherals subsystem 906, such as a global navigation satellite system (GNSS) (e.g., GPS receiver), a temperature sensor, a biometric sensor, magnetometer, or other sensing device, to facilitate related functionalities.

Camera subsystem 920 and optical sensor 922, e.g., a charged coupled device (CCD) or a complementary metal-oxide semiconductor (CMOS) optical sensor, may be utilized to facilitate camera functions, such as recording photographs and video clips. Camera subsystem 920 and optical sensor 922 may be used to collect images of a user to be used during authentication of a user, e.g., by performing facial recognition analysis.

Communication functions may be facilitated through one or more wired and/or wireless communication subsystems 924, which may include radio frequency receivers and transmitters and/or optical (e.g., infrared) receivers and transmitters. For example, the Bluetooth (e.g., Bluetooth low energy (BTLE)) and/or WiFi communications described herein may be handled by wireless communication subsystems 924. The specific design and implementation of communication subsystems 924 may depend on the communication network(s) over which the user device 900 is intended to operate. For example, user device 900 may include communication subsystems 924 designed to operate over a GSM network, a GPRS network, an EDGE network, a WiFi or WiMax network, and a Bluetooth™ network. For example, wireless communication subsystems 924 may include hosting protocols such that device 900 may be configured as a base station for other wireless devices and/or to provide a WiFi service.

Audio subsystem 926 may be coupled to speaker 928 and microphone 930 to facilitate voice-enabled functions, such as speaker recognition, voice replication, digital recording, and telephony functions. Audio subsystem 926 may be configured to facilitate processing voice commands, voice-printing, and voice authentication, for example.

I/O subsystem 940 may include a touch-surface controller 942 and/or other input controller(s) 944. Touch-surface controller 942 may be coupled to a touch surface 946. Touch-surface 946 and touch-surface controller 942 may, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch surface 946.

The other input controller(s) 944 may be coupled to other input/control devices 948, such as one or more buttons, rocker switches, thumb-wheel, infrared port, USB port, and/or a pointer device such as a stylus. The one or more buttons (not shown) may include an up/down button for volume control of speaker 928 and/or microphone 930.

In some implementations, a pressing of the button for a first duration may disengage a lock of touch-surface 946; and a pressing of the button for a second duration that is longer than the first duration may turn power to user device 900 on or off. Pressing the button for a third duration may activate a voice control, or voice command, module that enables the user to speak commands into microphone 930 to cause the device to execute the spoken command. The user may customize a functionality of one or more of the buttons. Touch-surface 946 may, for example, also be used to implement virtual or soft buttons and/or a keyboard.

In some implementations, user device 900 may present recorded audio and/or video files, such as MP3, AAC, and MPEG files. In some implementations, user device 900 may include the functionality of an MP3 player, such as an iPod™ User device 900 may, therefore, include a 36-pin connector and/or 8-pin connector that is compatible with the iPod. Other input/output and control devices may also be used.

Memory interface 902 may be coupled to memory 950. Memory 950 may include high-speed random access memory and/or non-volatile memory, such as one or more magnetic disk storage devices, one or more optical storage devices, and/or flash memory (e.g., NAND, NOR). Memory 950 may store an operating system 952, such as Darwin, RTXC, LINUX, UNIX, OS X, Windows, or an embedded operating system such as VxWorks.

Operating system 952 may include instructions for handling basic system services and for performing hardware dependent tasks. In some implementations, operating system 952 may be a kernel (e.g., UNIX kernel). In some implementations, operating system 952 may include instructions for performing voice authentication.

Memory 950 may also store communication instructions 954 to facilitate communicating with one or more additional devices, one or more computers and/or one or more servers. Memory 950 may include graphical user interface instructions 956 to facilitate graphic user interface processing; sensor processing instructions 958 to facilitate sensor-related processing and functions; phone instructions 960 to facilitate phone-related processes and functions; electronic messaging instructions 962 to facilitate electronic messaging-related process and functions; web browsing instructions 964 to facilitate web browsing-related processes and functions; media processing instructions 966 to facilitate media processing-related functions and processes; GNSS/Navigation instructions 968 to facilitate GNSS and navigation-related processes and instructions; and/or camera instructions 970 to facilitate camera-related processes and functions.

Memory 950 may store application (or "app") instructions and data 972, such as instructions for the apps described above in the context of FIGS. 1-7. Memory 950 may also store other software instructions 974 for various other software applications in place on device 900.

In the foregoing specification, specific embodiments have been described. However, one of ordinary skill in the art appreciates that various modifications and changes can be made without departing from the scope of the invention as set forth in the claims below. For example, although the invention has been described and illustrated in connection with a school, it is not intended to be so limited. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

While various embodiments have been described above, it should be understood that they have been presented by way of example and not limitation. It will be apparent to persons skilled in the relevant art(s) that various changes in form and detail may be made therein without departing from the spirit and scope. In fact, after reading the above description, it will be apparent to one skilled in the relevant art(s)

how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

The invention claimed is:

1. A computing system comprising:
a processor; and
a non-transitory computer-readable storage device storing computer-executable instructions, the instructions operable to causing the processor to perform operations comprising:
receiving an electrocardiogram (ECG) signal from a mobile automated external defibrillator (AED) unit;
filtering the ECG signal with a bandpass filter to generate an output signal;
identifying two or more peaks in the output signal;
calculating a cross-correlation energy for each of the two or more peaks;
calculating a self-correlation energy for each of the two or more peaks;
generating a correlation value for the ECG signal based on the cross-correlation energy and the self-correlation energy each of the two or more peaks; and
determining, based on the correlation value, whether a shock is required wherein,
the operations comprise administering a shock to a subject based on the generated correlation value.

2. The computing system of claim 1, wherein filtering the ECG signal comprises filtering the ECG signal with a first bandpass filter and a second bandpass filter.

3. The computing system of claim 2, wherein the first bandpass filter operates between 6 and 18 Hz and the second bandpass filter operates between 14 and 26 Hz.

4. The computing system of claim 2, wherein each of the first and second bandpass filters provide two outputs as the output signal.

5. The computing system of claim 4, wherein each of the first and second bandpass filters generate a real signal and an imaginary signal.

6. The computing system of claim 1, wherein calculating the cross-correlation energy comprises calculating a cross correlation energy between each peak and a plurality of other peaks of a same type.

7. The computing system of claim 1, wherein calculating the self-correlation energy comprises:
calculating a self-correlation energy for each peak of a pair of peaks;
multiplying the self-correlation energy for each peak; and
generating a square root of the product.

8. The computing system of claim 1, wherein generating the correlation value comprises:
summing the cross-correlation energies;
summing the self-correlation energies; and
dividing the sum of the cross-correlation energies by the sum of the self-correlation energies.

9. The computing system of claim 1, wherein the operations comprise causing a recommendation to be displayed on a user interface of a user device based on the generated correlation value.

10. A computer-implemented method performed by at least one processor comprising:
receiving an electrocardiogram (ECG) signal from a mobile automated external defibrillator (AED) unit;
filtering the ECG signal with a bandpass filter to generate an output signal;
identifying two or more peaks in the output signal;
calculating a cross-correlation energy for each of the two or more peaks;
calculating a self-correlation energy for each of the two or more peaks;
generating a correlation value for the ECG signal based on the cross-correlation energy and the self-correlation energy each of the two or more peaks; and
determining, based on the correlation value, whether a shock is required; and
administering a shock to a subject based on the generated correlation value.

11. The computer-implemented method of claim 10, wherein filtering the ECG signal comprises filtering the ECG signal with a first bandpass filter and a second bandpass filter.

12. The computer-implemented method of claim 11, wherein the first bandpass filter operates between 6 and 18 Hz and the second bandpass filter operates between 14 and 26 Hz.

13. The computer-implemented method of claim 11, wherein each of the first and second bandpass filters provide two outputs as the output signal.

14. The computer-implemented method of claim 13, wherein each of the first and second bandpass filters generate a real signal and an imaginary signal.

15. The computer-implemented method of claim 10, wherein calculating the cross-correlation energy comprises calculating a cross correlation energy between each peak and a plurality of other peaks of a same type.

16. The computer-implemented method of claim 10, wherein calculating the self-correlation energy comprises:
calculating a self-correlation energy for each peak of a pair of peaks;
multiplying the self-correlation energy for each peak; and
generating a square root of the product.

17. The computer-implemented method of claim 10, wherein generating the correlation value comprises:
summing the cross-correlation energies;
summing the self-correlation energies; and
dividing the sum of the cross-correlation energies by the sum of the self-correlation energies.

18. The computer-implemented method of claim 10 comprising causing a recommendation to be displayed on a user interface of a user device based on the generated correlation value.

* * * * *